US011389400B2

(12) United States Patent
Batchinsky et al.

(10) Patent No.: US 11,389,400 B2
(45) Date of Patent: Jul. 19, 2022

(54) AEROSILIZATION OF STEM CELLS OR STEM CELL DERIVATIVES FOR PULMONARY DELIVERY

(71) Applicant: Qool Therapeutics, Inc., Menlo Park, CA (US)

(72) Inventors: Andriy Batchinsky, San Antonio, TX (US); Ben Antebi, Helotes, TX (US); Brendan M. Beely, San Antonio, TX (US); Leopoldo C. Cancio, San Antonio, TX (US); Amir Belson, Savyon (IL); Beverly Huss, Menlo Park, CA (US); Edward J. Hayes, San Jose, CA (US); Jeff G. Haydon, Menlo Park, CA (US)

(73) Assignee: The Government of The United States, as Represented by The Secretary of the Army, Fort Detrick, MD (US)

( * ) Notice: Subject to any disclaimer, the term of this patent is extended or adjusted under 35 U.S.C. 154(b) by 544 days.

(21) Appl. No.: 16/045,046

(22) Filed: Jul. 25, 2018

(65) Prior Publication Data
US 2018/0325817 A1 Nov. 15, 2018

Related U.S. Application Data

(63) Continuation of application No. PCT/US2017/015494, filed on Jan. 27, 2017.

(60) Provisional application No. 62/289,071, filed on Jan. 29, 2016.

(51) Int. Cl.
*A61K 9/00* (2006.01)
*A61K 35/545* (2015.01)
*A61K 35/28* (2015.01)
*A61F 7/12* (2006.01)
*A61F 7/00* (2006.01)
*A61M 11/00* (2006.01)
*A61P 11/00* (2006.01)
*A61M 16/20* (2006.01)
*A61M 16/14* (2006.01)
*A61K 35/50* (2015.01)

(52) U.S. Cl.
CPC ............ *A61K 9/0075* (2013.01); *A61F 7/00* (2013.01); *A61F 7/12* (2013.01); *A61K 9/0078* (2013.01); *A61K 35/545* (2013.01); *A61M 11/00* (2013.01); *A61F 2007/0064* (2013.01); *A61K 35/28* (2013.01); *A61K 35/50* (2013.01); *A61M 11/001* (2014.02); *A61M 16/14* (2013.01); *A61M 16/201* (2014.02); *A61M 2202/0437* (2013.01); *A61M 2202/064* (2013.01); *A61M 2205/3368* (2013.01); *A61M 2205/3606* (2013.01); *A61M 2205/366* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 4,051,847 A | 10/1977 | Henkin | |
| 8,100,123 B2 | 1/2012 | Belson | |
| 8,281,786 B2 | 10/2012 | Belson | |
| 8,402,968 B2 | 3/2013 | Belson | |
| 11,020,269 B2 * | 6/2021 | Mirizzi | ................. A61M 16/14 |
| 2005/0103340 A1 * | 5/2005 | Wondka | .............. A61M 16/021 128/204.18 |
| 2008/0057040 A1 * | 3/2008 | Crook | ...................... A01N 1/02 424/93.7 |
| 2008/0230053 A1 * | 9/2008 | Kraft | ..................... A61M 15/00 128/200.23 |
| 2008/0308101 A1 * | 12/2008 | Spandorfer | ......... A61M 15/008 128/203.14 |
| 2010/0112068 A1 | 5/2010 | Boyden et al. | |
| 2011/0129897 A1 | 6/2011 | Glover et al. | |
| 2012/0167878 A1 | 7/2012 | Belson et al. | |
| 2013/0085554 A1 | 4/2013 | Belson et al. | |
| 2014/0060534 A1 | 3/2014 | Belson | |
| 2014/0065240 A1 | 3/2014 | Mitsialis et al. | |
| 2014/0341998 A1 * | 11/2014 | Onoue | ............... A61K 31/4418 424/489 |

(Continued)

FOREIGN PATENT DOCUMENTS

| | | |
|---|---|---|
| CN | 102271741 A | 12/2011 |
| CN | 107530187 A | 1/2018 |
| WO | WO-2014109793 A1 | 7/2014 |

(Continued)

OTHER PUBLICATIONS

Asmussen, et al. Human mesenchymal stem cells reduce the severity of acute lung injury in a sheep model of bacterial pneumonia. Thorax(2014): thoraxjnl-2013.
Averyanov, et al. Comparative effects of inhaled and intravenous mesenchymal stem cells in bleomycin-induced pulmonary fibrosis in rabbits. (2013): 226.
Chang, et al. Intratracheal transplantation of human umbilical cord blood-derived mesenchymal stem cells dose-dependently attenuates hyperoxia-induced lung injury in neonatal rats. Cell transplantation 20.11-12 (2011): 1843-1854.
Chimenti, et al. Pre-treatment with mesenchymal stem cells reduces ventilator-induced lung injury. European respiratory journal(2012): erj01532-2011.

(Continued)

*Primary Examiner* — Robert T. Crow
*Assistant Examiner* — John P Nguyen
(74) *Attorney, Agent, or Firm* — Wilson Sonsini Goodrich & Rosati

(57) ABSTRACT

A treatment system delivers a breathing gas and frozen stem cells or other biologic particles (FBP) to a bronchus of a lung of a patient in order to treat lung and other conditions. The breathing gas and the FBP are usually delivered through separate lumens. The FBP may be delivered concurrently with other frozen particles, such as frozen saline particles (FSP). The FBP/FSP will remain frozen at all times from preparation to delivery, and will thaw only after they are released into the lung.

22 Claims, 10 Drawing Sheets

(56) References Cited

U.S. PATENT DOCUMENTS

| | | |
|---|---|---|
| 2015/0068525 A1 | 3/2015 | Belson |
| 2015/0320836 A1 | 11/2015 | Itkin-Ansari et al. |

FOREIGN PATENT DOCUMENTS

| | | |
|---|---|---|
| WO | WO-2015130900 A1 | 9/2015 |
| WO | WO-2016138045 A1 | 9/2016 |
| WO | WO-2016192202 A1 | 12/2016 |

OTHER PUBLICATIONS

Curley, et al. Effects of intratracheal mesenchymal stromal cell therapy during recovery and resolution after ventilator-induced lung injury. Anesthesiology: The Journal of the American Society of Anesthesiologists 118.4 (2013): 924-932.

Curley, et al. Mesenchymal stem cells enhance recovery and repair following ventilator-induced lung injury in the rat.Thorax67.6 (2012): 496-501.

Danchuck, et al. Human multipotent stromal cells attenuate lipopolysaccharide-induced acute lung injury in mice via secretion of tumor necrosis factor-α-induced protein 6. Stem cell research & therapy 2.3 (2011): 27.

Davies, et al. Aerosol delivery of DNA/liposomes to the lung for cystic fibrosis gene therapy. Human Gene Therapy Clinical Development 25.2 (2014): 97-107.

Devaney, et al. Human mesenchymal stromal cells decrease the severity of acute lung injury induced by $E.\ coli$ in the rat. Thorax (2015): thoraxjnl-2015.

Di-Liang, et al. Autologous transplantation of adipose-derived stromal cells ameliorates ventilator-induced lung injury in rats. Journal of translational medicine 11.1 (2013): 179.

Gupta, et al. Intrapulmonary delivery of bone marrow-derived mesenchymal stem cells improves survival and attenuates endotoxin-induced acute lung injury in mice. The Journal of Immunology 179.3 (2007): 1855-1863.

Hayes, et al. Therapeutic efficacy of human mesenchymal stromal cells in the repair of established ventilator-induced lung injury in the rat. Anesthesiology: The Journal of the American Society of Anesthesiologists 122.2 (2015): 363-373.

International Search Report and Written Opinion mailed Apr. 28, 2017 for International Application No. PCT/US2017/015494.

"IPRP for WO2017132609 Jul. 31, 2018".

Kim, et al. Intratracheal transplantation of human umbilical cord blood-derived mesenchymal stem cells attenuates *Escherichia coli*-induced acute lung injury in mice. Respiratory research 12.1 (2011): 108.

Kumar, et al. Distal airway stem cells yield alveoli in vitro and during lung regeneration following H1N1 influenza infection. Cell 147.3 (2011): 525-538.

Makela, et al. Safety and biodistribution study of bone marrow-derived mesenchymal stromal cells and mononuclear cells and the impact of the administration route in an intact porcine model. Cytotherapy 17.4 (2015): 392-402.

Mei, et al. Prevention of LPS-induced acute lung injury in mice by mesenchymal stem cells overexpressing angiopoietin 1. PLoS medicine 4.9 (2007): e269.

Oritz, et al. Interleukin 1 receptor antagonist mediates the antiinflammatory and antifibrotic effect of mesenchymal stem cells during lung injury. Proceedings of the National Academy of Sciences 104.26 (2007): 11002-11007.

Pati, et al. Bone marrow derived mesenchymal stem cells inhibit inflammation and preserve vascular endothelial integrity in the lungs after hemorrhagic shock. PloS one 6.9 (2011): e25171.

Rojas, et al. Human adult bone marrow-derived stem cells decrease severity of lipopolysaccharide-induced acute respiratory distress syndrome in sheep. Stem cell research & therapy 5.2 (2014): 42.

Rubin, et al. Emerging aerosol drug delivery strategies: from bench to clinic. Advanced drug delivery reviews75 (2014): 141-148.

Sun, et al. Intrapulmonary delivery of human umbilical cord mesenchymal stem cells attenuates acute lung injury by expanding CD4+ CD25+ Forkhead Boxp3 (FOXP3)+ regulatory T cells and balancing anti-and pro-inflammatory factors. Cellular Physiology and Biochemistry 27.5 (2011): 587-596.

Tibboel, et al. Intravenous and intratracheal mesenchymal stromal cell injection in a mouse model of pulmonary emphysema. COPD: Journal of Chronic Obstructive Pulmonary Disease 11.3 (2014): 310-318.

Wilson, et al. Mesenchymal stem (stromal) cells for treatment of ARDS: a phase 1 clinical trial. The Lancet Respiratory Medicine 3.1 (2015): 24-32.

Wittwer, et al. Mesenchymal stem cell pretreatment of non-heart-beating-donors in experimental lung transplantation. Journal of cardiothoracic surgery 9.1 (2014): 151.

Xu, et al. Mesenchymal stem cell- based angiopoietin- 1 gene therapy for acute lung injury induced by lipopolysaccharide in mice. The Journal of pathology 214.4 (2008): 472-481.

Zheng, et al. Treatment of acute respiratory distress syndrome with allogeneic adipose-derived mesenchymal stem cells: a randomized, placebo-controlled pilot study. Respiratory research 15.1 (2014): 39.

Zuo, et al. p63+ Krt5+ distal airway stem cells are essential for lung regeneration. Nature517.7536 (2015): 616.

\* cited by examiner

FIG. 1B

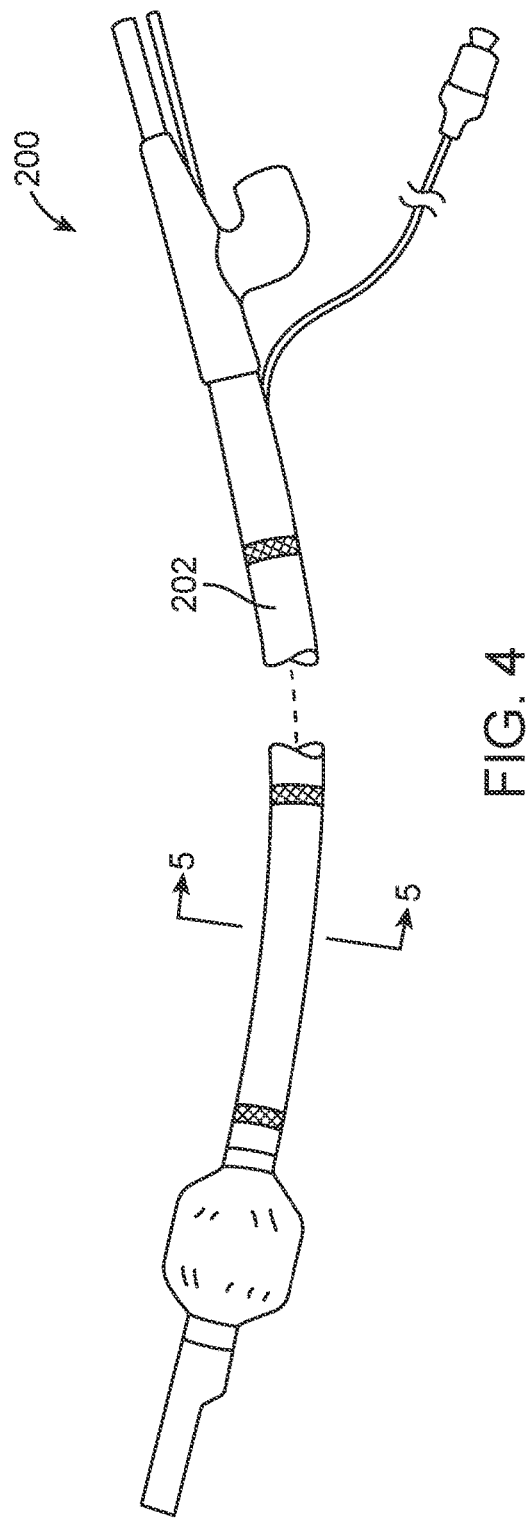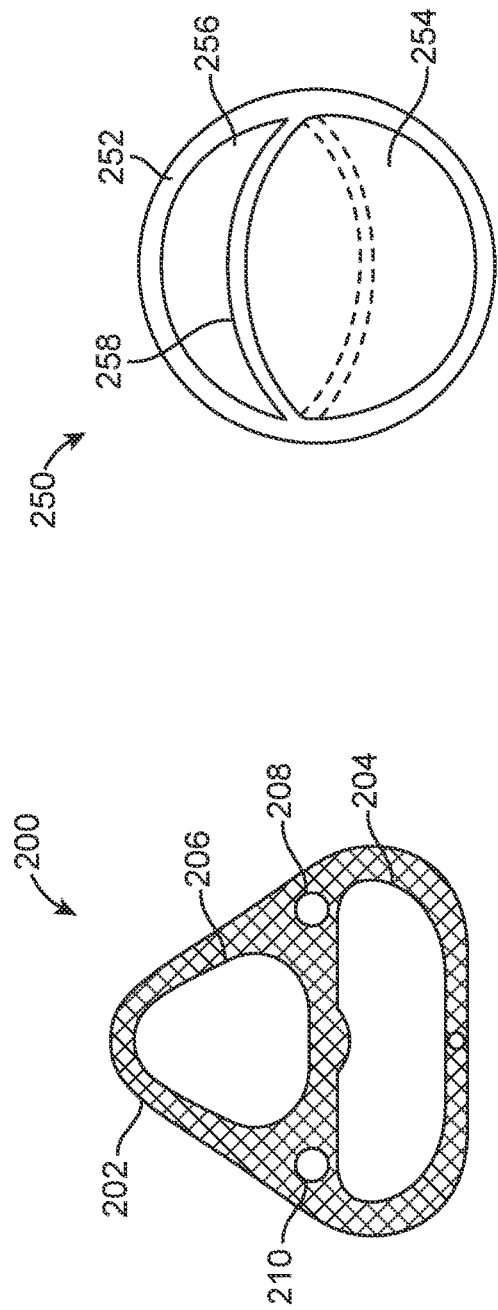
FIG. 4
FIG. 5
FIG. 6

AEROSILIZATION OF STEM CELLS OR STEM CELL DERIVATIVES FOR PULMONARY DELIVERY

CROSS-REFERENCE TO RELATED APPLICATIONS

This application is a continuation of PCT Application No. PCT/US17/15494, filed Jan. 27, 2017, which claims the benefit of U.S. provisional application No. 62/289,071, filed on Jan. 29, 2016, the full disclosures of which are incorporated herein by reference.

STATEMENT AS TO FEDERALLY SPONSORED RESEARCH

This invention was made with the support of the United States government under CRADA Department of Defense MRMC and Defense Innovation Unit Experimental (DIUx) Solicitation Number: RPP Number DIUx-17-R-0008, and CRADA # MRMC Control Number W81XWH-16-0130 by Department of Defense MRMC and Defense Innovation Unit Experimental (DIUx).

BACKGROUND OF THE INVENTION

1. Field of the Invention

The following inventions relate generally to compositions, apparatus, and methods for preparing and delivering stem cells and other viable cells and cellular substances to humans and other animals. In particular, the inventions relate to systems and methods for freezing stem cells and delivering frozen stem cells to a patient's lungs.

Stem cell-based therapies have been at the forefront of preclinical and clinical studies. A stem cell is a cell that can self-renew indefinitely as well as give rise to different types of specialized cells. Generally, stem cells can be classified into three main categories: embryonic stem cells (ESCs), induced pluripotent stem cells (iPSCs), and adult stem cells (ASCs).

Adult stem cells (ASCs) are multipotent stem cells found at different tissues of the body throughout the life of an organism. At minimum, ASCs can differentiate to specialized cells of the tissue from which they were obtained. They replenish tissues through multiple mechanisms and reside in certain organs once believed of possessing no regenerative potential, such as the brain and heart. There are many types of ASCs, but most prevalent ones include: hematopoietic stem cells, endothelial stem cells, neural stem cells, mammary stem cells, intestinal stem cells, distal airway stem cells (DASCs), and mesenchymal stem cells (MSCs).

Adult stem cells, and specifically MSCs obtained from both bone marrow and adipose tissue, have shown great promise for treating various diseases. Of particular interest to the present invention, the unique ability of MSCs to modulate the immune and inflammatory response, thwart infection, and regenerate tissue via differentiation or paracrine mechanisms make them particularly attractive for the management of lung injuries in combat casualties and civilian populations, and MSCs have proven beneficial for mitigating acute lung injury as demonstrated in numerous small animal models, a few large animal models, and human clinical trials. Recently, new resident lung stem cells, termed DASCs, have been discovered following induction of acute respiratory distress disorder (ARDS) in mice and were shown to regenerate human alveolar structures in vitro and migrate to sites of parenchymal injury in vivo, thus establishing their essential role in intrinsic lung regeneration.

Generally, stem cells can be delivered either locally or systemically. Local administration includes the targeted transplantation into the organ/tissue but requires invasive surgery and may be location-dependent. More often, systemic administration via the intravenous route is employed. Systemic administration is also problematic and may lead to serious clinical complications, such as pulmonary emboli. Moreover, following systemic administration, the biodistribution of cells is also unknown, as cells may migrate, distribute, and entrap in other, unwanted end-organs. Finally, it is known that following administration, approximately 90% of transplanted cells are not viable due to physical stresses, inflammation, and hypoxia that occur in vivo. Currently, local lung transplantation of stem cells and their derivatives has been performed in various preclinical animal studies via direct instillation into the trachea (intratracheally). While promising, direct instillation suffers from certain drawbacks, such as limiting delivery of the cells to the upper airways, and clinical adoption may be limited or prevented due to edema and secretions which restrict the upper airways.

Aerosolization and inhalation are recognized as an effective combination for the delivery drugs and biologics beyond the upper airways to the deepest areas of the lungs. Bronchodilators, antifungals, antibiotics, gene therapies, and insulin are all deliverable via inhalation. Stem cell delivery via inhalation has also been proposed, e.g. US2014/0065240 and US2011/0129897 which suggest that various drugs and biologics, including micronized stem cell preparations, can be delivered by conventional inhalation protocols, such as metered-dose inhalers, dry powder inhalers, and nebulizers. These references, however, do not consider how stem cell viability might be retained during micronization and subsequent delivery via inhalation.

Therefore, there remains a strong unmet clinical need to develop improved compositions, apparatus, and methods for preparing and delivering stem cells and other viable cells and cellular substances to humans and other animals. In particular, it would be desirable to provide methods and compositions which result in improved viability of stem cells and other cells and cellular components during preparation and delivery to improve the effectiveness of the associated cell-based therapies. At least some of these objectives will be met by the inventions described and claimed herein.

2. Description of the Background Art

US2014/0065240 and US2011/0129897 have been described above. The following U.S. Patents and U.S. Patent Publications, owned by an assignee of the present application, describe the delivery of ice particles to a patient's lungs, optionally with drugs, to induce hypothermia through heat exchange with a patent's lungs: U.S. Pat. Nos. 8,402,968; 8,281,786; 8,100,123; 2012/0167878; 20140060534; 2015/0068525, and WO2016/138,045, the full disclosures of which are incorporated herein by reference. Local lung transplantation of stem cells or their derivatives has been performed in various preclinical animal studies via direct instillation into the trachea (intratracheally). See, Kim, E. S., et al., Intratracheal transplantation of human umbilical cord blood-derived mesenchymal stem cells attenuates *Escherichia coli*-induced acute lung injury in mice. Respir Res, 2011. 12: p. 108; Curley, G. F., et al., Effects of intratracheal mesenchymal stromal cell therapy during recovery and resolution after ventilator-induced lung injury. Anesthesiology, 2013. 118(4): p. 924-32; Tibboel, J., et al., Intravenous and intratracheal mesenchymal stromal cell injection in a mouse model of pulmonary emphysema. COPD, 2014. 11(3): p. 310-8; and Gupta, N., et al., Intrapulmonary delivery of bone marrow-derived mesenchymal stem cells improves survival and attenuates endotoxin-induced acute lung injury in mice. J Immunol, 2007. 179(3): p. 1855-63. Other relevant publications discussing the preparation and therapeutic uses of stem cells include: Devaney, J., et al., Human mesenchymal stromal cells decrease the severity of acute lung injury induced by E. coli in the rat. Thorax, 2015. 70(7): p. 625-35; Hayes, M., et al., Therapeutic efficacy of human mesenchymal stromal cells in the repair of established ventilator-induced lung injury in the rat. Anesthesiology, 2015. 122(2): p. 363-73; Sun, J., et al., Intrapulmonary delivery of human umbilical cord mesenchymal stem cells attenuates acute lung injury by expanding CD4+CD25+ Forkhead Boxp3 (FOXP3)+ regulatory T cells and balancing anti- and pro-inflammatory factors. Cell Physiol Biochem, 2011. 27(5): p. 587-96; Chang, Y. S., et al., Intratracheal transplantation of human umbilical cord blood-derived mesenchymal stem cells dose-dependently attenuates hyperoxia-induced lung injury in neonatal rats. Cell Transplant, 2011. 20(11-12): p. 1843-54; Curley, G. F., et al., Mesenchymal stem cells enhance recovery and repair following ventilator-induced lung injury in the rat. Thorax, 2012. 67(6): p. 496-501; Chimenti, L., et al., Pre-treatment with mesenchymal stem cells reduces ventilator-induced lung injury. Eur Respir J, 2012. 40(4): p. 939-48; Liang, Z. D., et al., Autologous transplantation of adipose-derived stromal cells ameliorates ventilator-induced lung injury in rats. J Transl Med, 2013. 11: p. 179; Pati, S., et al., Bone marrow derived mesenchymal stem cells inhibit inflammation and preserve vascular endothelial integrity in the lungs after hemorrhagic shock. PLoS One, 2011. 6(9): p. e25171; Mei, S. H., et al., Prevention of LPS-induced acute lung injury in mice by mesenchymal stem cells overexpressing angiopoietin 1. PLoS Med, 2007. 4(9): p. e269; Xu, J., et al., Mesenchymal stem cell-based angiopoietin-1 gene therapy for acute lung injury induced by lipopolysaccharide in mice. J Pathol, 2008. 214(4): p. 472-81; Danchuk, S., et al., Human multipotent stromal cells attenuate lipopolysaccharide-induced acute lung injury in mice via secretion of tumor necrosis factor-alpha-induced protein 6. Stem Cell Res Ther, 2011. 2(3): p. 27; Ortiz, L. A., et al., Interleukin 1 receptor antagonist mediates the antiinflammatory and antifibrotic effect of mesenchymal stem cells during lung injury. Proc Natl Acad Sci USA, 2007. 104(26): p. 11002-7; Makela, T., et al., Safety and biodistribution study of bone marrow-derived mesenchymal stromal cells and mononuclear cells and the impact of the administration route in an intact porcine model. Cytotherapy, 2015. 17(4): p. 392-402; Asmussen, S., et al., Human mesenchymal stem cells reduce the severity of acute lung injury in a sheep model of bacterial pneumonia. Thorax, 2014. 69(9): p. 819-25; Rojas, M., et al., Human adult bone marrow-derived stem cells decrease severity of lipopolysaccharide-induced acute respiratory distress syndrome in sheep. Stem Cell Res Ther, 2014. 5(2): p. 42; Wilson, J. G., et al., Mesenchymal stem (stromal) cells for treatment of ARDS: a phase 1 clinical trial. Lancet Respir Med, 2015. 3(1): p. 24-32; Zheng, G., et al., Treatment of acute respiratory distress syndrome with allogeneic adipose-derived mesenchymal stem cells: a randomized, placebo-controlled pilot study. Respir Res, 2014. 15: p. 39; Kumar, P. A., et al., Distal airway stem cells yield alveoli in vitro and during lung regeneration following H1N1 influenza infection. Cell, 2011. 147(3): p. 525-38; Zuo, W., et al., p63(+)Krt5(+) distal airway stem cells are essential for lung regeneration. Nature, 2015. 517(7536): p. 616-20; Davies, L. A., et al., Aerosol delivery of DNA/liposomes to the lung for cystic fibrosis gene therapy. Hum Gene Ther Clin Dev, 2014. 25(2): p. 97-107; Rubin, B. K. and R. W. Williams, Emerging aerosol drug delivery strategies: from bench to clinic. Adv Drug Deliv Rev, 2014. 75: p. 141-8; Averyanov, A.e.a. Comparative effects of inhaled and intravenous mesenchymal stem cells in bleomycin-inducedpulmonary fibrosis in rabbits. in European Respiratory Society Annual Congress. 2013; Wittwer, T., et al., Mesenchymal stem cell pretreatment of non-heart-beating-donors in experimental lung transplantation. J Cardiothorac Surg, 2014. 9: p. 151; and Finlay, W. H., 8—Jet nebulizers, in The Mechanics of Inhaled Pharmaceutical Aerosols, W. H. Finlay, Editor. 2001, Academic Press: London. p. 175-220.

SUMMARY OF THE INVENTION

The present invention provides stem cell and other biologic compositions and methods and apparatus for the pulmonary delivery of such biologic compositions. In particular, the present invention provides frozen cellular and other biologic compositions, particularly including stem cells, and methods for their preparation. The present invention further provides methods and systems for delivering the frozen biologic compositions to a patient's lungs for local treatment of lung conditions, such as acute lung injury due to smoke inhalation, acute respiratory distress syndrome (ARDS), cystic fibrosis, emphysema, chronic occlusive pulmonary disease (COPD), and other pulmonary-based diseases or injuries. As used in the claims and elsewhere herein, the phrase "biologic compositions" refers to all types of therapeutic cellular and other biologic substances, particularly including stem cells, as well as cellular derivatives, such as conditioned media (CM) and extracellular vesicles (EVs), and the like. In addition to delivering stem cells and other cellular compositions, at least some of the preparation and delivery methods and systems of the present invention may find use with other viable and non-viable biologic compositions, such as cell lysate and/or their CM and EVs, referred to collectively hereinafter and in the claims as "biologics." By "frozen," it is meant that the cellular and other biologic compositions are lowered to a temperature that causes at least a portion of an aqueous content of the cell or other biologic to freeze, i.e. undergo a phase change from liquid water to solid ice.

At least most of the frozen aqueous component of the frozen cells and other biologics will remain frozen at all times after freezing until delivery to and release into a patient's lung, particularly into a main bronchus or a branching bronchus of the lung. In particular, the frozen stem cells and other biologics useful in the present invention will not include compositions which are lyophilized (freeze-dried) at the time of use, i.e. following an initial freezing of the aqueous content. That is, it is an important aspect of the present invention that the retained frozen aqueous content of the cellular and other biologic compositions thaw or melt at a time as close to release into the lungs as possible, preferably after release as will be described in more detail below. In some cases, however, it may be possible to reconstitute lyophilized or other dried stem cell compositions and other biologics with an aqueous phase prior to freezing by the methods described herein.

For delivery into the deep regions of the lungs, it is desirable that the frozen stem cells have a mean dimeter below 100 µm, usually below 80 µm, often below 40 µm, and sometimes below 10 μm. Exemplary size ranges are from 100 μm to 4 μm, often from 80 μm to 10 μm, frequently from 40 μm to 10 μm, and sometimes from 20 μm to 10 μm. Non-cellular biologics will be much smaller, often in the range from 10 nm to 1000 nm. Many intact stem cells and other biologics will have mean diameters above this desired size, it may be necessary or desirable to powderize or micronize the cells or biologics prior to or after freezing, usually after freezing. The frozen, optionally micronized, stem cells and other biologics may then be delivered to the patient, typically through a breathing tube where the frozen stem cells or other biologics are entrained in a breathing gas which ventilates the patient so that the cellular and other biologic compositions are carried into the deep regions of the lungs by the patient's natural or induced respiration cycle. Optionally, the frozen stem cells and other biologics may be entrained with other materials, such as other frozen particles which help maintain the temperature to inhibit pre-mature thawing of the frozen stem cells and other biologics. Alternatively or additionally, the added frozen particles may further induce hypothermia locally in the lungs and/or systemically which is believed to enhance the uptake and/or efficacy of the biological compositions.

Use of the frozen stem cells and other biologics of the present invention has several advantages over pulmonary delivery methods including, but not limited to, the fact that freezing can prevent necrosis and/or apoptosis (i.e., programmed cell death) of the stem cells. By further employing a low energy micronization technology, the stem cell compositions can be powderized to an optimum size range for delivery while preventing or inhibiting cell and/or protein damage of the type caused by high energy ultrasonic systems. These advantages help protect the stem cells while they are being delivered to the target location for deposition, maximizing therapeutic and treatment potential. Additionally, phase change of the frozen stem cells and other biologics as they are released can assist in a targeted or "localized" administration of stem cells. By delivering the stem cells while in the frozen phase, they are protected until they approach and reach their intended target, which is a primary benefit of this invention.

A first method of the present invention provides for delivering frozen biologic particles (FBP) to the lungs of a patient. A breathing gas stream is delivered to a bronchus of a lung of the patient; and FBP from an FBP source are also delivered to the lung bronchus. By entraining the FBP in the breathing gas, the FBP may be carried by the breathing gas into the lower lung.

In specific aspects of the first method, the FBP are frozen while in the FBP source and remain frozen until they are released into the lung. In further specific aspects, the breathing gas and the FBP are delivered through separate lumens of a breathing tube, or alternatively may be delivered through a common lumen in a breathing tube. Usually, the breathing gas and the FBP are delivered during at least a portion of some of the patient's inhalation cycles but not during the patient's exhalation cycles.

Delivery of the FBP to the lung may comprise providing a bolus of FBP and flowing a volume of carrier gas through the bolus to entrain the FBP in the flowing carrier gas to produce an FBP-entrained flowing carrier gas stream which is delivered to the lung through a FBP lumen separate from the breathing gas. Usually, at least a portion of the carrier gas from the FBP-entrained flowing carrier gas stream is vented to produce a gas reduced FBP-entrained flowing carrier gas stream, wherein said gas reduced FBP-entrained flowing carrier gas stream is delivered to the FBP lumen.

A second method of the present invention provides for delivery of frozen biologic particles (FBP) to the lungs of a patient. A plurality of boluses of FBP are dispersed into a flowing carrier gas to entrain the FBP in the flowing carrier gas to produce an FBP-entrained flowing carrier gas stream. The FBP-entrained flowing carrier gas stream is delivered to a lung of the patient simultaneously with a separate breathing gas stream in synchrony with the patient's inhalation cycle.

In specific aspects of the second method, a single bolus is delivered with each inhalation, where an amount of FBP is controlled by adjusting the inhalation rate delivered by a ventilator. The amount of FBP delivered to the patient is typically controlled by adjusting an amount of FBP in individual boluses. A tidal volume of breathing gas delivered to the patient comprises a sum of a breathing gas volume and a carrier gas volume delivered on each inhalation cycle. Usually, the tidal volume of total breathing gas delivered to the patient is adjusted to a target level by venting a portion of the carrier gas from the FBP-entrained flowing carrier gas stream after dispersing the FBP therein and before delivering the FBP-entrained flowing carrier gas stream and separate breathing gas stream to the lung of the patient to produce a reduced FBP-entrained flowing carrier gas stream. The target level of tidal volume of total breathing gas is typically in the range from 150 ml to 1000 ml per inhalation cycle.

A system according to the present invention for delivering frozen biologic particles (FBP) to the lungs of a patient comprises a tubular device configured for advancement through the patient's trachea to the bronchus. The tubular device has one or more lumens therethrough, and an external FBP source is configured to deliver FBP through the at least one lumen of the tubular device to the bronchus. An external breathing gas source is configured to deliver FBP through the at least one lumen of the tubular device to the bronchus so that the FBP become entrained in the breathing gas and are carried by the breathing gas to lower regions of the patient's lung.

In specific aspects of the system, the FBP and the breathing gas are both connected to be delivered through a common lumen in the breathing tube. Alternatively, the FBP and the breathing gas may both be connected to be delivered through separate lumens in the breathing tube.

In further specific aspects, the system comprises a controller, where the controller may be configured to adjust the amount or rate of delivery of FBP from the external FBP source through the at least one lumen. The controller may alternatively or further be configured to adjust the amount or rate of delivery of breathing gas from the external breathing gas source through the at least one lumen.

The systems of the present invention typically further comprising external source of frozen saline particles (FSP) configured to be delivered through the at least one lumen of the tubular device to the bronchus, wherein the controller is configured to adjust the amount or rate of delivery of FSP delivery from the external FSP source through the at least one lumen. The external FBP source may comprise a means for providing a bolus of FBP and flowing a volume of carrier gas through the bolus to entrain the FBP in the flowing carrier gas to produce an FBP-entrained flowing carrier gas stream. The external FBP source will usually further comprise a means for venting a portion of the carrier gas from the FBP-entrained flowing carrier gas stream to produce a gas reduced FBP-entrained flowing carrier gas stream, wherein said gas reduced FBP-entrained flowing carrier gas stream is delivered to the FBP lumen.

In an alternate aspect, the system of the present invention may further comprise a controller, configured to control venting of the carrier gas to produce a tidal volume of total breathing gas delivered to the patient in the range from 150 ml to 1000 ml per inhalation cycle. For example, the controller may be configured to vent at least 50% of the gas originally present in the FBP-entrained flowing carrier gas stream to produce the gas reduced FBP-entrained flowing carrier gas stream.

The present invention further provides compositions of matter comprising a biologic material having an aqueous phase, wherein the aqueous phase is frozen so that the material is formed into flowable particles having a size in the range from 4 μm to 100 μm and wherein the particles are capable of being carried into the lower lung of a patient by normal or induced respiration. The biologic materials in these compositions of matter typically comprise stem cells which remain viable after being released in a lung while still frozen and thereafter carried into the lower lung by normal or induced respiration.

In a further method according to the present invention, frozen biologic particles (FBP) are produced by obtaining, growing or otherwise providing viable biologic cells. The cells are frozen in saline in the presence of cryopreservative(s), protein(s) to provide growth factors, and a suitable growth medium. The biologic cells may comprise stem cells; the proteins may comprise human serum albumin and/or fetal bovine serum; and the cryopreservative may comprise DMSO, polyvinylpyrrolidone (PVP), glycerol, polyethylene glycol (PEG), ethylene glycol, and/or trehalose. The frozen cells are collected and maintained under conditions where they and retain a frozen aqueous phase.

Typically, freezing comprises cooling the cells at a controlled rate in the range from 0.5° C./min to 2° C./min to form pellets. The cells may be frozen into pellets, large blocks of frozen cells, or the like, and will usually be comminuted or powderized to a form suitable for pulmonary delivery to a patient while maintained in a frozen condition. Alternatively, freezing may comprise spraying a mist of the stem cells into a liquid gas. In all cases, agglomerations, pellets, and/or blocks of the frozen cells may be comminuted into particles having a mean diameter in the range from 4 μm to 100 μm, although the size can be significantly below this range for non-cellular biologics. For example, large frozen blocks of the cells may be broken into fragments and comminuting the fragments into particles having a mean diameter in the range from 4 μm to 100 μm.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1B illustrates an alternative method for producing FBP by spraying a liquid which carries stem cells or other biologics into a liquid nitrogen bath.

FIGS. 4 and 5 illustrate a combined ventilator-PIT useful in the delivery of FBP/FSP to a patient.

FIG. 6 illustrates a combined ventilator-PIT having a movable internal septum useful in the delivery of FBP/FSP to a patient.

DETAILED DESCRIPTION OF THE INVENTION

Figure 1:
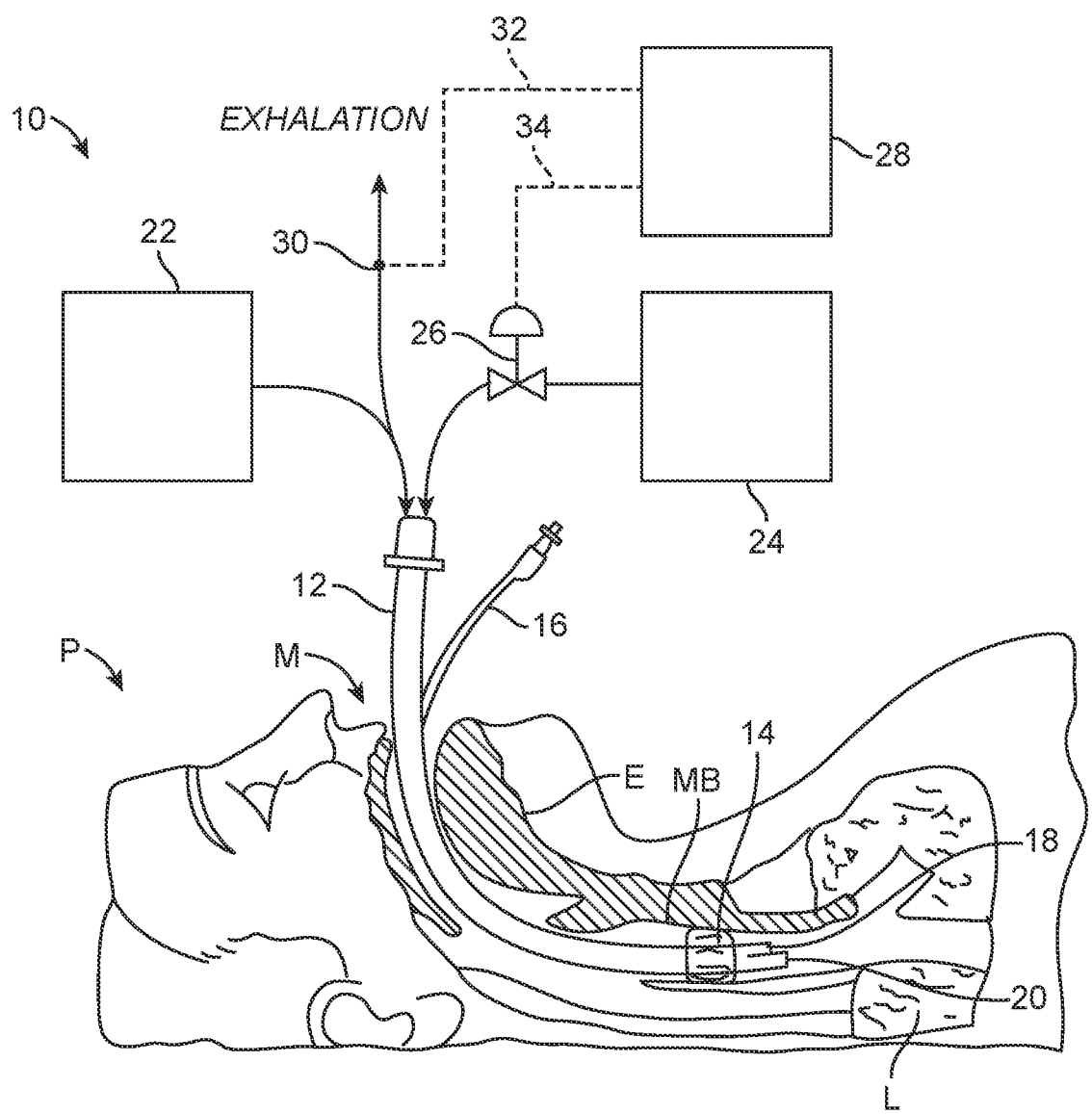
FIG. 1 illustrates a system comprising an endotracheal tube having both a particle delivery lumen and a breathing gas lumen for delivering a mist of frozen biologic particles (FBP) and optionally frozen saline particles (FSP) to a patient.

Stem Cell and Biologics Preparation.

Harvested stem cells of any type or source (blood, placenta, bone marrow, fat, umbilical-cord, or otherwise) are prepared for freezing. Stem cells may also be obtained from induced pluripotent cells. Stem cells are typically cryopreserved in 10% dimethyl sulfoxide (DMSO) in saline together with a protein (e.g., human serum albumin) or a protein mixture (e.g., fetal bovine serum) to sustain stem cell viability. The DMSO serves as the cryoprotectant to inhibit the formation of intracellular ice crystals which would rupture the cell membrane during the freezing process. Other strategies may also be employed to prepare the biologics if deemed appropriate. Lower DMSO concentrations and/or other cryoprotectants, such as polyvinylpyrrolidone (PVP), glycerol, polyethylene glycol (PEG), ethylene glycol, or trehalose, could also be used, and the protein mixture could be modified for particular cell and biologic types and/or particular preparation processes. Other variations may be employed for particular cell and biologic types to enhance viability during freezing, comminution, and delivery such as reducing or eliminating saline, adding plasma to inhibit ice crystal formation within the cell walls.

Freezing Process.

The prepared stem cells are cooled at a controlled rate (1° C./min) by placing a vial containing the stem cells in a receptacle maintained at −80° C. The vial of stem cells is left overnight at −80° C. to produce frozen stem cell pellets, typically having a grain or particle size in the range from 1 mm to 2 cm, often in the range from 1 cm to 2 cm. The pellets may then be further processed or may be transferred to liquid nitrogen (−196° C.) for long-term storage. Other cooling protocols employing different cooling rates and final temperatures may alternatively be used depending on the cell type and other factors.

Different freezing methods can also be employed. For example, instead of forming pellets, freezing may be performed to produce large blocks of frozen cells. The blocks could be fragmented using percussive or other means prior to comminution.

A further exemplary freezing process would spray the stem cells or other biologics in a dilute aqueous phase through a misting nozzle directly into an $LN_2$ bath. It is believed that the resulting rapid freezing would generate an amorphous solid (frozen) phase of smaller particles comprising individual or small agglomerations of cells. The frozen cells would then be extracted from the from the LN2 bath.

Comminution or Micronization.

The frozen pellets produced by the freezing process are micronized in a conventional comminution system of the type used for biological materials, such as a cryogenic ball mill, a cryogenic jet mill, or a cryogenic hammer mill. For example, as shown in FIG. 1A, cryogenic micronization may be accomplished in a jet mill (sometimes called a spiral jet mill), using a spiraling gas obtained from a liquid nitrogen ($LN_2$) source in the head space gas. In the case of a hammer mill, a $LN_2$ cooling may be applied to the casing and material feed. Once the desired size is achieved, currently estimated to be approximately 4 µm to 100 µm (additional exemplary ranges set forth above), the powder is either collected and transferred to a delivery system or stored at cryogenic temperatures in a range from 0° C. to 270° C. using $LN_2$, $LO_2$, LHe, frozen $CO_2$ (dry ice), or the like until time of use. The mechanical micronization techniques relied on in the present invention are believed to produce the powder in such a way as to minimize damage to cells. In contrast, the use of ultrasonic or similar technologies can cause more substantial damage to the cells due to the high amount of energy delivered to the substance while being atomized.

Alternate Preparation Protocols.

Figure 1B:
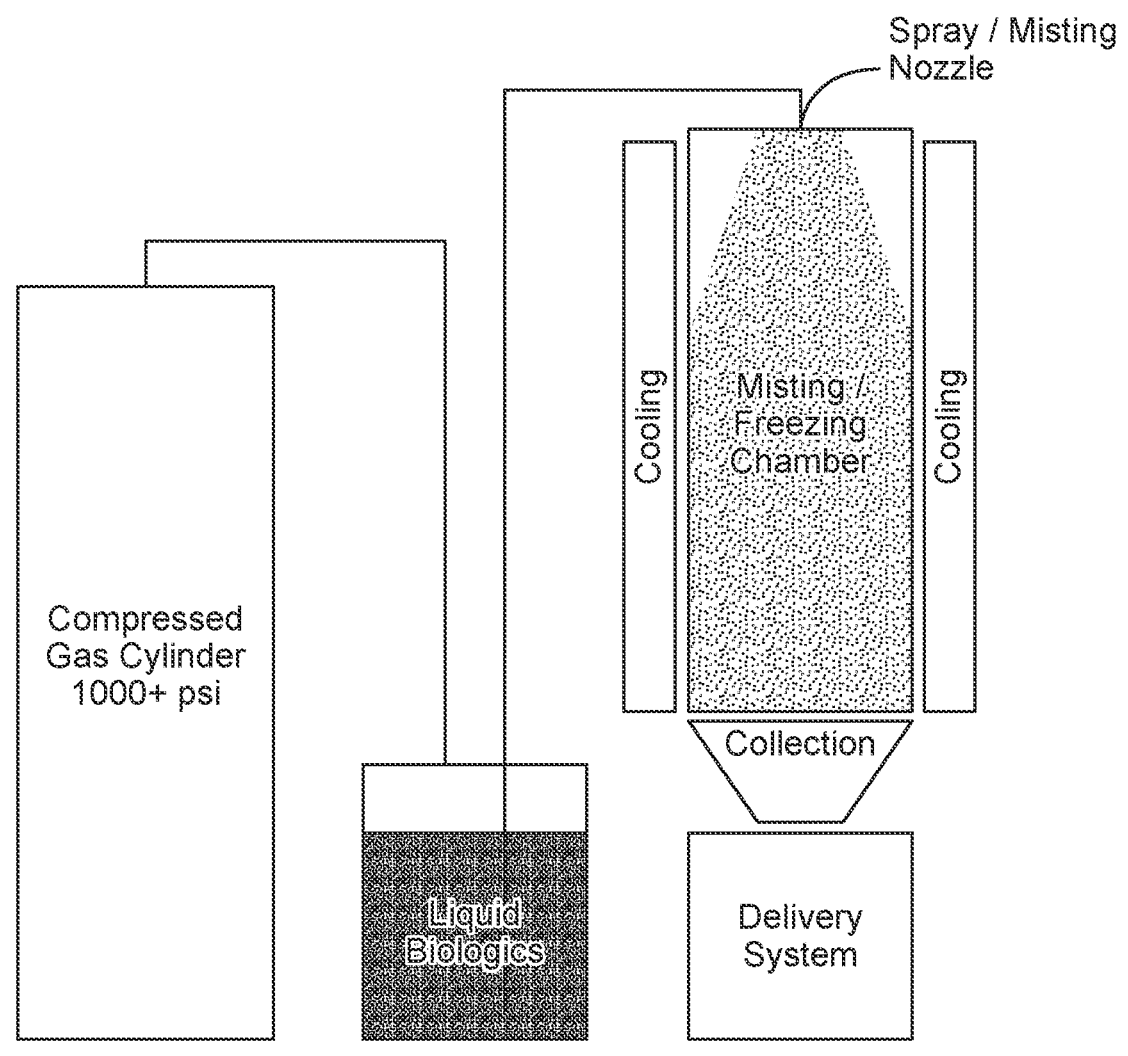

The frozen stem cell and other biologic powders of the present invention may be prepared by alternative protocols that minimize exposure to thawing and potential to the stem cells and biologics by using liquid micronization technology and subsequently immediately freezing the resultant micronized stem cell aerosol liquid. The liquid stem cell and biologic preparations prepared as described above are micronized by known technologies, such as nebulizers and techniques for generating cryogenic frozen saline particles previously disclosed in U.S. Pat. Nos. 8,402,968; 8,281,786; 8,100,123; US2012/0167878; US20140060534; US2015/0068525; and WO2016/138,045, the full disclosures of which have been previously incorporated herein by reference. The frozen stem cell and other biologic particles could be prepared and stored in a cryogenic slurry prior to use, or could be prepared and used in an in-line manner as illustrated in FIG. 1B. As shown in FIG. 2, in-line freezing can be performed without collection in $LN_2$, reducing the number of preparation steps although potentially increasing delivery system complexity.

Delivery System.

Figure 1A:
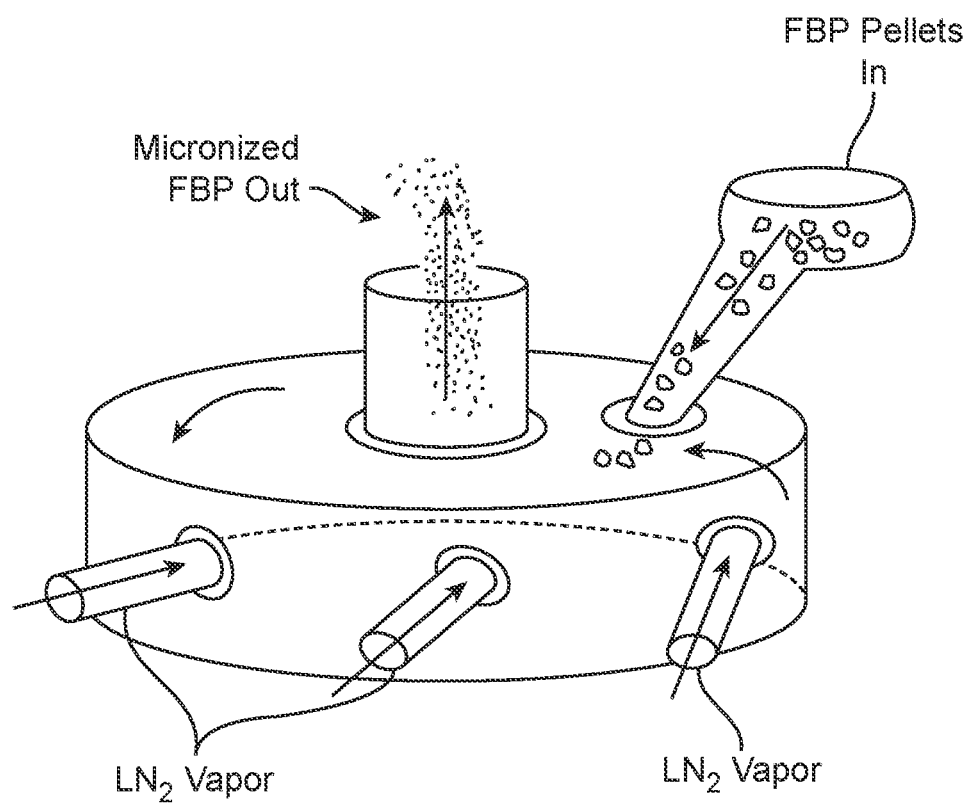
FIG. 1A illustrates a spiral jet mill suitable for micronizing FBP.
Figure 2:
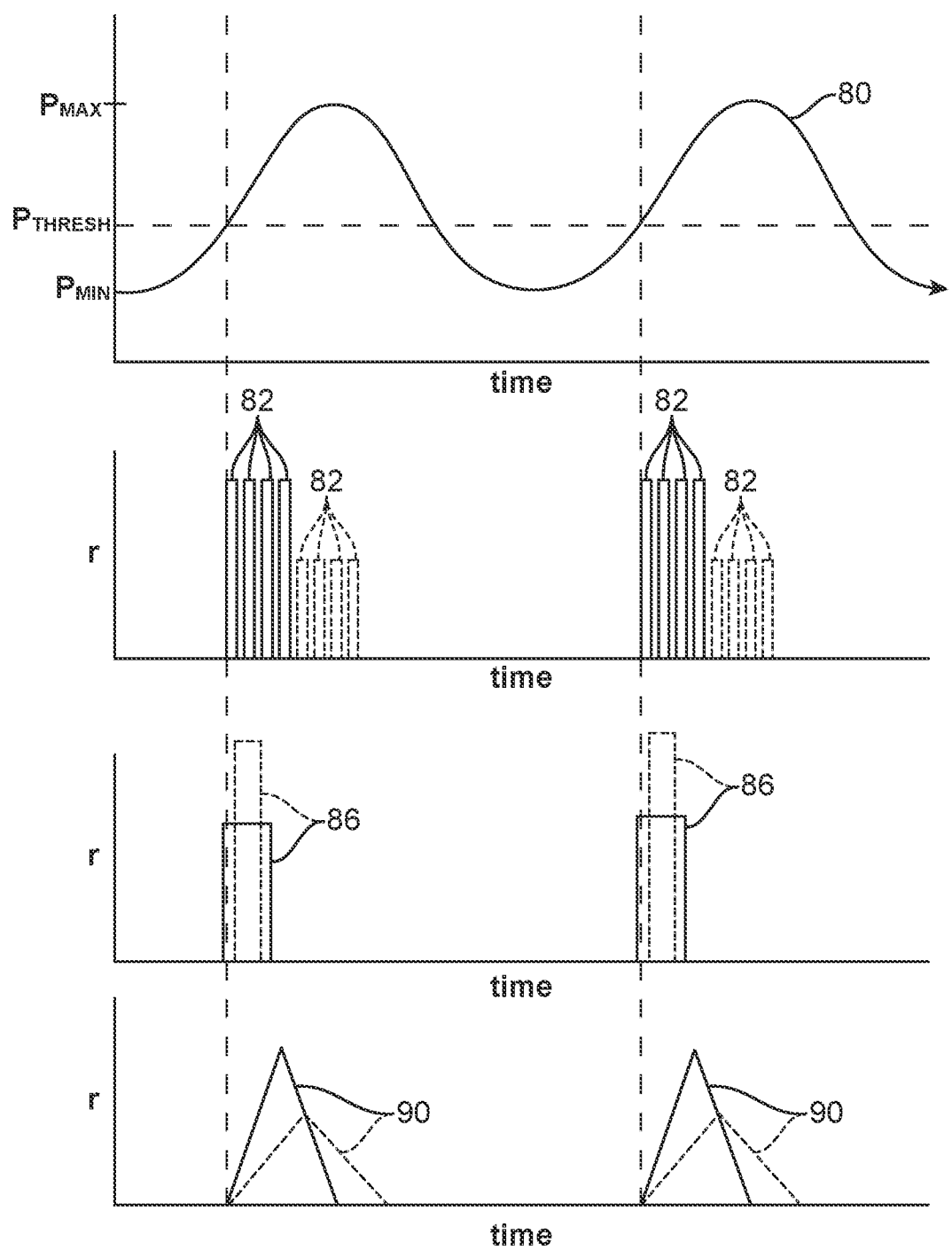
FIG. 2 is a graph illustrating exemplary delivery patterns useful in the delivery of FBP/FSP to a patient.

An exemplary system 10 according to the present invention for delivering the frozen stem cell and biologic compositions of the present invention is illustrated in FIG. 1. Many aspects of this and other exemplary frozen particle delivery systems as are described herein are shown in greater detail in WO2016/0192202, which has been previously incorporated herein by reference. The delivery systems of the present invention generally include a particle source or generator 24 which provides the frozen stem cells or other biologic particles to be delivered (referred to collectively hereinafter as frozen biologic particles or "FBP"). The particle source or generator 24 may also provide frozen saline or other aqueous particles (referred to collectively hereinafter as frozen saline particles or "FSP") to be delivered concurrently with the FBP. The system 10 further includes a mechanical respiration system 22 and a tubular device 12 similar to an endotracheal tube for accessing the main bronchus of a patient P. This system 10 is configured to maintain the FBP in a frozen state with minimum or no thawing until the FBP are released into the approximately 37° C., high relative humidity environment of a patient's lung where they will thaw and melt as they are entrained into the inspired breathing gas and carried into the deeper lung.

The tubular device 12 delivers the breathing gas and the FBP and optionally FSP directly to the patient's P lungs L. The tubular device 12 will be configured for intraoral placement through the patient's esophagus and trachea and will include a cuff 14 which can be inflated via an inflation tube 16 to isolate a distal end of the tubular device within a main bronchus MB of the patient in a manner conventional for endotracheal tubes. The tubular device 12 is shown as a single body or extrusion having at least two lumens terminating in separate distal ports 18 and 20 to separately deliver the breathing gas and the FBP, respectively, to the patient's lungs L. The distal ports 18 and 20 will typically but not necessarily be axially or otherwise separated to inhibit flow back of the FBP into the breathing lumen which can result in melting and re-freezing of the FBP which, in turn, can cause clogging of the breathing lumen. Usually the breathing gas port will be disposed upstream (toward the mouth M) in the main bronchus MB to minimize any direct contamination. Also, as will be described below, the FBP and FSB are preferably delivered only during the patient's inhalation cycle so the risk of FBP/FSP entering the exhalation lumen during the patient's exhalation cycle is reduced. In other embodiments as described below, the tubular device may include an FBP and optionally FSP delivery conduit which is separate from a breathing gas delivery conduit. The separate FBP/FSP delivery conduit and breathing gas delivery conduit may be arranged coaxially, in parallel, with relative helical winds, or the like.

After the patient P has been intubated with the tubular device 12, breathing air will be provided in a conventional manner from a ventilator or other breathing source 22. In addition, successive boluses of FBP/FSP will be delivered from the FBP/FSP source 24 through a valve 26. As shown, the valve 26 controls the FB/FSP flow, but in other embodiments described below a separate "puff" valve will provide bursts of carrier gas which entrains the FBP/FSP to mix with the breathing gas and deliver the FBP into the lungs. A controller 28 senses the temperature of the patient's exhalation through a temperature sensor 30 located at an outlet of the tubular device 12.

Usually, the FBP and optionally FSP will be delivered during only a portion of the inhalation cycle. For example, as shown in FIG. 2, inhalation or ventilation pressure P of the patient may be monitored, for example by using a pressure sensor measuring the output pressure of the ventilator 22, as shown at the top of FIG. 2. The pressure will typically be a sine wave 80 with a minimum occurring between successive inhalations/ventilations. As shown in a second graph from the top of FIG. 2, the FBP may be delivered in a series of bursts or puffs 82 coming usually in the middle of the inhalation/ventilation cycle. The number of bursts or puffs and amount of ice in each individual burst or puff may be varied and the greater the number and/or volume of each puff will, of course, translate into greater cooling of the patient.

While use of the puffs is desirable since it helps prevent clogging of the ice delivery components of the system it is not necessary. The frozen particles may alternatively be delivered in a single spike 86 where the amount of frozen particles in the spike may be varied by controlling either the duration or the rate of the spike as shown in solid line and broken line, respectively. Similarly, the burst need not be in the form of a square wave but could also have a time-varying profile as shown at the bottom of FIG. 2. Again, the duration or rate of the delivery will determine the total amount of frozen particles delivered in any given spike or release.

Figure 3:
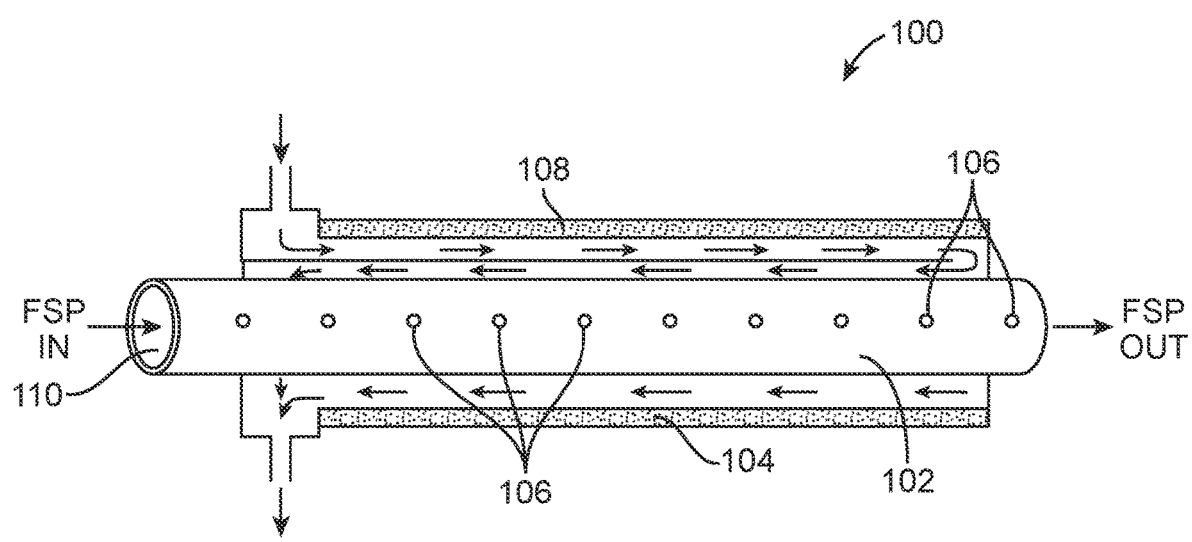
FIG. 3 is a schematic view of a patient interface tube (PIT) having a cooling jacket useful in the delivery of FBP/FSP to a patient.

As shown in FIG. 3, a patient interface tube (PIT) 100 can be used as for the endotracheal delivery of the FBP/FSP and is the to provide (1) a lumen for frozen biologic/saline delivery, (2) an annular cooling space, and (3) a temperature monitoring system. A coolant, such as refrigerated air or gas (which could be the same as the breathing gas) is circulated through the annular cooling space 104 disposed coaxially about an FBP/FSP delivery conduit 102. The temperature of the FBP/FSP delivery lumen can be monitored with one or more temperature sensors 106 and can be precisely controlled by metering the flow rate of the coolant through the annular cooling space and/or by controlling the temperature of the coolant entering the annular cooling space. The PIT 100 will be insulated to prevent damage to the patient's trachea and can be constructed of metallic or polymeric materials. Furthermore, upon exiting the annular cooling space, the refrigerated air may be utilized for cooling other components required for the procedure or experiment. The temperature monitoring sensors 106 may be thermocouples, thermistors, RTD's, or the like and may be placed along the length of the FBP delivery conduit 102, usually along an inner surface thereof, at pre-selected intervals or locations to provide for temperature monitoring and/or active, feedback control. The FBP are delivered through an FBP delivery lumen 110 in the FBP delivery conduit 102, and an insulating layer 108 will usually be provided over the exterior of the FBP delivery conduit 102 to protect the patient's trachea and esophagus from the low temperature of the annular cooling space 104.

The PIT may be formed as an integrated unit to provide both breathing gas delivery and FBP delivery in a single device having at least two isolated lumens. Such integrated PIT-ventilator tube embodiments may be actively heated, actively cooled, or both actively heated and actively cooled to ensure the FBP delivery lumen remains at the proper temperature for frozen saline delivery (as noted above) and that the breathing gas is delivered at a desired temperature as well.

An exemplary multi-lumen integrated ventilator tube-PIT 200 is shown in FIGS. 4 and 5 and includes a polymeric body 202 similar in design and dimensions to a conventional endotracheal tube. The PIT body 202 is usually formed as a triangular extrusion, as shown in FIG. 5, which facilitates passage through the larynx to the lungs. The larynx which holds the patient's vocal cords has a generally triangular periphery when expanded and the portion if the body 202 which must pass through the larynx may have a periphery similar in size and shape so that the internal area of the body available for creation of the FBP lumen, the ventilator (breathing gas) lumen, and any other lumens may be maximized.

The body 202 will typically have at least several lumens including one lumen 204 for ventilating the patient using a conventional mechanical ventilation machine and another lumen 206 for delivery of FBP during the inhalation cycle of the patient. The ventilation lumen 204 and the FBP lumen 206 will usually be isolated from each other over their entire lengths to limit mixing of the FBP with warm humid air during exhalation of the patient. Moisture in warm exhalation air can freeze on the walls of the FBP lumen, and the warm air can also partially melt the FBP to create further free liquid in the FBP lumen. Liquid from both sources can re-freeze on the FBP lumen wall which in turn can clog the lumen and significantly reduce performance of the system.

Optionally, one or more internal walls or septa within a multi-lumen extruded PTI body may be formed to be repositioned in response to changes in pressure differential across the wall or septum. As shown in FIG. 6, a PIT-ventilator tube 250 having an extruded polymeric body 252 can have an FBP delivery lumen 254 and a ventilation lumen 256 separated and isolated by a movable septum 258. During inhalation, when the breathing gas pressure is less than the FBP delivery pressure, the septum 258 will shift to create a larger cross-section area for the FBP delivery lumen 254, as shown in full line. Conversely, during exhalation when no FBP are being delivered, the exhalation pressure will be greater, shifting the position of the septum 258 to maximize the area of the ventilation lumen 256 which will reduce back pressure.

Referring now to FIG. 10, a FPB/FSP generator and controller 350 useful for delivering FBP/FSP through the PIT's described above will typically comprises a plurality of individual components to generate and control the number of individual FBP/FSP boluses delivered to any of the PIT and ventilator tube assemblies described hereinbefore. The FBP generator and controller 350 will also usually provide cooling gasses to other portions of the system as needed and as described elsewhere herein. Typically, the ventilator 352 will be a separate system component, often being a commercial unit which has been modified to be controlled in combination with the FBP/FSP generator. In particular, a pressure sensor 353 may be connected to measure the output pressure of the ventilator 352 and provide a pressure signal to the controller 370 of the FBP generator and controller 350. The pressure sensor 353 may be part of the commercial system or may be added to the commercial system. In either case, it will be used to monitor the inhalation and exhalation cycles generated by the ventilator. Typically, the controller 370 will also be electronically interfaced with the ventilator 352 so that the operational parameters of the ventilator can be adjusted by the controller 370. In other embodiments, the ventilator may be provided as part of the FBP generator and control system itself so that all components of both the FBP generator and ventilator may be included in a single unit.

The FBP/FSP generator and controller 350 will include a gas source 372 to provide pressurized gas for dispersing the FBP and delivering the dispersed FBP to the PIT. The gas source 372 will be non-toxic and typically comprise a conventional breathing gas, such as air, oxygen, heliox, or any gas of the type which may be used in conventional patient ventilation. The gas will typically be provided in a pressurized gas bottle, but use of a compressor for generating compressed air or other breathing gases will also be possible. Pressurized gas from the gas source 372 is delivered through a heat exchanger 374, typically a liquid nitrogen cooler, which lowers the temperature of the gas before it is used to disperse the FBP. At least most of the gas from the heat exchanger 374 will be delivered to a "puff" valve 376 and will be used to disperse the FBP, but a side stream 377 can also be taken off to provide for various other cooling functions within the system, for instance cooling of the PIT illustrated in FIG. 3.

The puff valve 376 is controlled by controller 370 so that it will open to allow pressurized gas to flow during the patient's inhalation cycle in order to generate FBP for delivery to the patient during the inhalation cycle. Specifically, gas from the puff valve 376 flows into an FBP dispersion unit 380, which is best described in connection with FIG. 11 below, and the resulting boluses of FBP will then usually flow into a blocking valve 382 which forms part of a blocking and vent valve unit 386. The blocking valve 382 will be opened simultaneously with the puff valve 376 and will be closed during the exhalation cycle of the patient to inhibit backflow of exhalation gases into the PIT and other portions of the cooling system.

A vent valve 384 which forms part of the blocking and vent valve unit 386 serves a different purpose. The vent valve 384 will also be opened during at least a portion of the inhalation cycle when FBP are being delivered in the flow of puff gases through the particular generator 380. It has been found that full dispersion of the FBP requires a relatively high volume of dispersion gas. While the dispersion gases are non-toxic, and will often be the same gas as the breathing gas delivered by the ventilator, is undesirable that the dispersion gases form a majority of the tidal volume to be delivered to the patient during each inhalation cycle. The vent valve allows a portion of the excess dispersion gases to be vented from the system. Once the FBP are dispersed in the puff of dispersion gases after having passed through the particle dispersion unit 380, it is possible to vent a significant portion of these "carrier" or dispersion gases from the flowing FBP stream. Thus, by providing a vent valve 384, typically in combination with a flow control orifice (not shown), a significant portion of the carrier or dispersion gasses may be bled from the system before being delivered to the patient. Typically more than 50%, often more than 60%, and sometimes as much 80% of more of the dispersion gasses may be vented. In this way, the majority of breathing gas delivered to the patient will come from the ventilator 352 which may be controlled to maintain patient ventilation in a more normal manner and may also be used to deliver anesthetics, or for other therapeutic purposes. The gasses leaving the blocking/vent valve unit 386 will then be delivered to the PIT as shown in more detail hereinbelow.

Gasses from the ventilator 352 may also optionally be passed through a heat exchanger 375, which again will typically be a liquid nitrogen heat exchanger. The heat exchanger used for cooling the breathing gasses may be the same as heat exchanger 374 use to cool the dispersion gasses. The heat exchanger 375 is provided at the output of the ventilator, it is preferred that a bypass 377 be provided for the exhalation gasses that are being returned to the ventilator.

Figure 8:
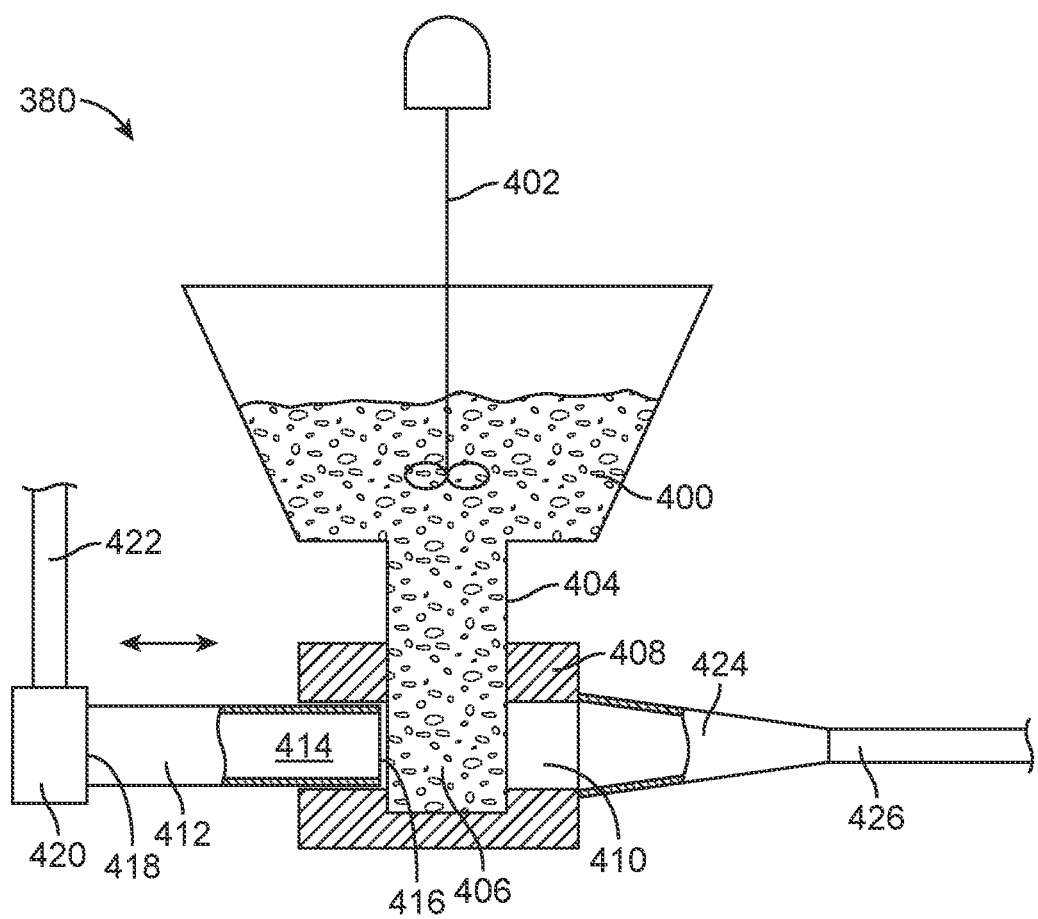
FIG. 8 illustrates a bolt and breech assembly for injecting measured boluses of FBP into a flowing gas stream.

Referring now to FIG. 8, the FBP/FSP particle dispersion unit 380 will typically include an FBP/FSP hopper 400 which is maintained in a cold environment such as in a liquid nitrogen cooler or thermoelectric or other refrigerator. Optionally, the hopper can be configured to receive FBP directly from a misting/freezing channel as illustrated and discussed above in connection with FIG. 1B. A mixer 402 helps the FBP flow downward through a chute 404 into a measuring receptacle 406 within a block or breech 408. The block 408 includes a transverse passage 410 which intersects the chute 404 so that FBP fall into the portion of the chute within the passage 410 in a repeatable manner to provide a measured amount of FBP therein. A bolt 412 having a hollow bore 414 is mounted so that an open distal end 14 may be advanced into the measuring receptacle 406 to separate a measured portion of the FBP, as will be described in more detail below. The bolt as illustrated axially reciprocates, but rotating bolt systems may also be used. A proximal end 418 of the bolt 412 has a proximal fitting 420 which is connected to a flexible line 422 which receives the dispersion gas from the puff valve 376, seen in FIG. 10. A taper tube 422 is connected to the downstream end of the passage 410 in the block 408 so that FBP may be delivered to a line 426 which is connected to the blocking/vent valve assembly 386, again as shown in FIG. 10.

Figure 9A:
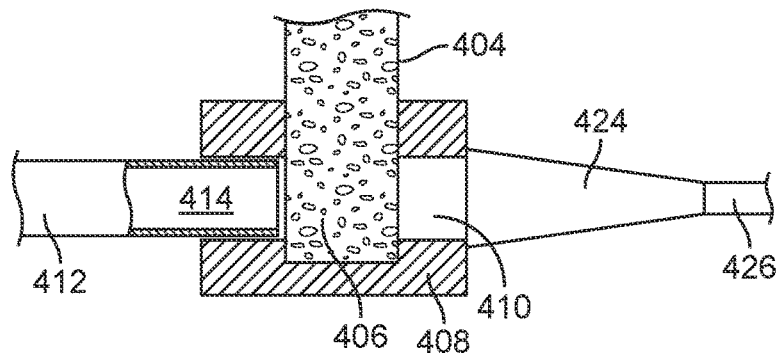
FIGS. 9A-9D illustrate the step-by-step use of the bolt and breech assembly of FIG. 8 for producing the boluses of FBP.
Figure 9B:
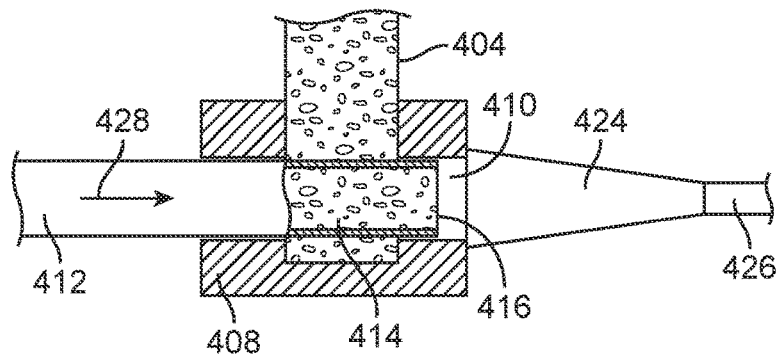

Referring now to FIGS. 9A-9D, the FBP/FSP particle dispersion unit 380 is shown at the beginning of its measurement and dispersion cycle in FIG. 9A. The bolt 412 is distally advanced in the direction of arrow 428 so that the open distal end 416 passes through and "cores" a portion of the FBP/FSP in the measuring receptacle 406.

Figure 7:
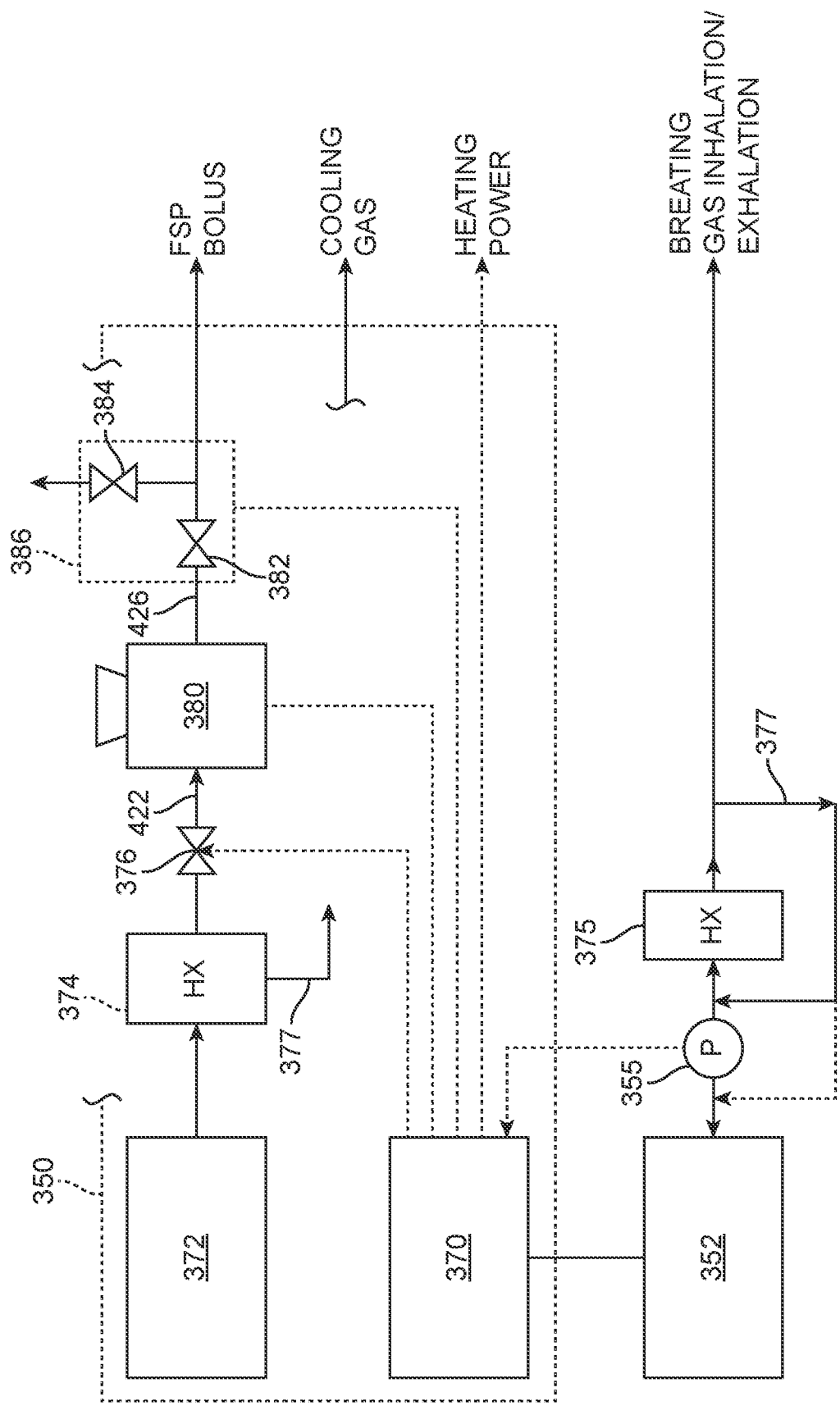
FIG. 7 illustrates a system for generating and controlling both an FBP stream and a breathing gas for delivery through the PIT's and ventilator tubes useful in the delivery of FBP/FSP to a patient.
Figure 9C:
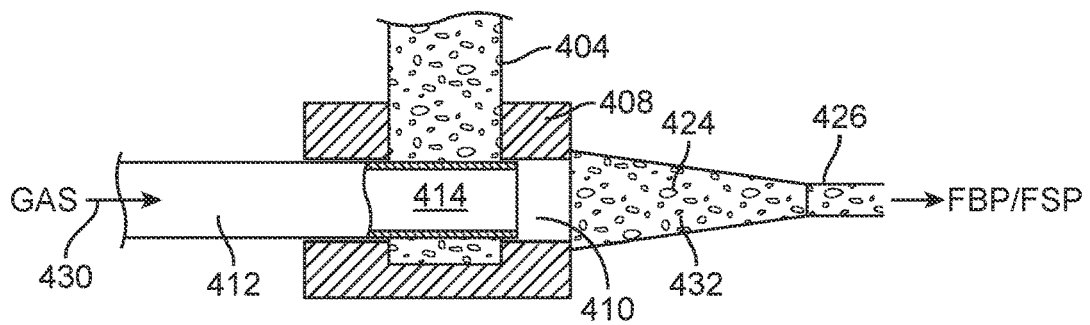

After the bolt 412 has passed through the measuring receptacle 406, advancement of the bolt is terminated, and puff valve 376 is opened to release a "puff" of dispersion gas through the line 422 and into the hollow bore 414 of the bolt 412 as shown by arrow 430 in FIG. 9C. The dispersion gas expels the FBP which had been present in the bore 414 so that a bolus 432 of the dispersed FBP is dispersed and advanced through the taper tube 424 and into the transfer tube 426 which leads to the blocking/vent valve assembly 386, as shown in FIG. 7.

Figure 9D:
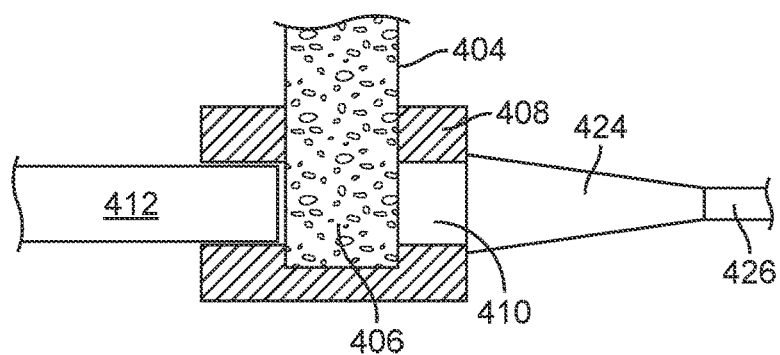

As shown in FIG. 9D, after bolus 432 of the FBP/FSP has been delivered, the bolt 412 may be retracted to its initial position up stream of the measuring receptacle 406, allowing additional FBP to fall by gravity into the measuring receptacle. The particle dispersion unit 380 is then ready for the next cycle of bolus generation which will typically be generated upon the next inhalation cycle of the patient by the controller 370.

Figure 10A:
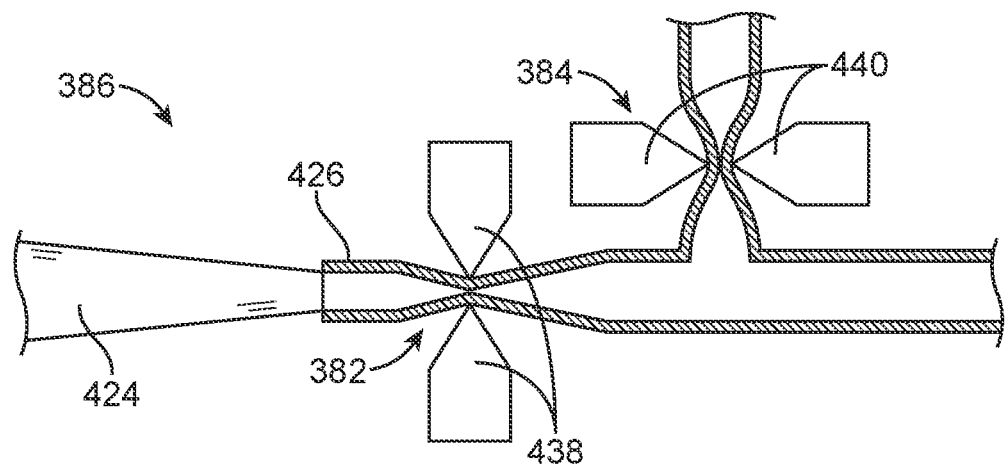
FIGS. 10A and 10B illustrate pinch-type vent and isolation valves that may be disposed downstream of the bolt and breech assembly of FIG. 8 for reducing the gas volume carrying the FBP and preventing back flow of exhalation gases, respectively.
Figure 10B:
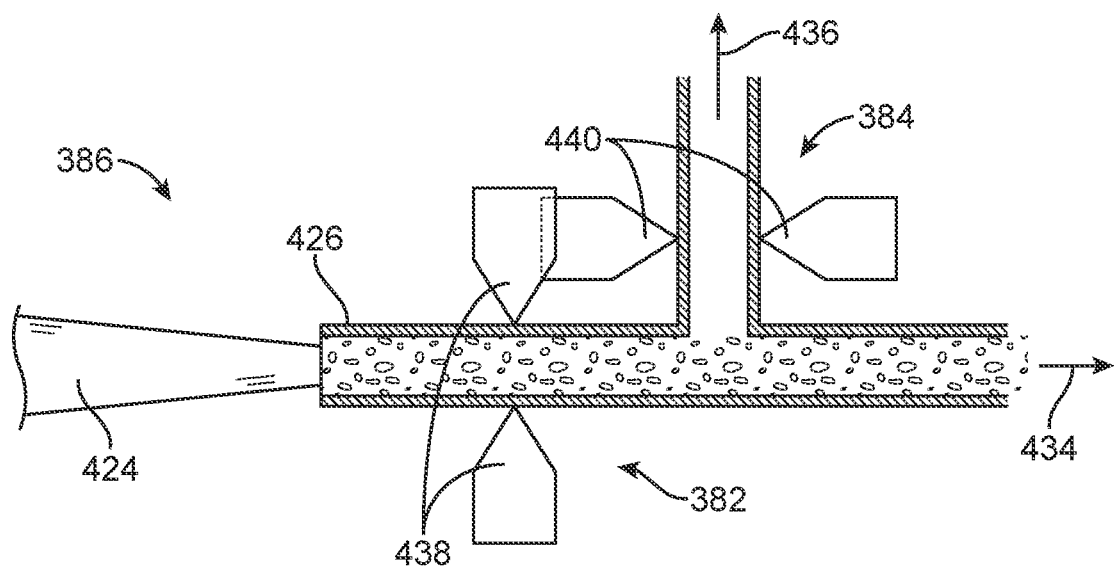

Referring now to FIGS. 10A-10B, exemplary embodiments for the blocking/vent valve unit 386 will be described. Both the blocking valve 382 and the vent valve 384 will typically be "pinch" valves including opposed pinching elements 438 and 440, respectively. The dispersion line 426 which receives the dispersed FBP/FSP from the particulate dispersion unit 380 will be a flexible tube so that the pinching elements 438 and 440 may be closed over the tube to selectively close the lumens through the tubes, as shown in FIG. 10A, or open said lumens, as shown in FIG. 10B. The valves 382 and 384 will both be closed and during the exhalation cycle of the patient, helping inhibit backflow of the exhalation gasses through the PIT and any other portions of the system. When delivering FBP/FSP into the inhalation gas, however, the valves 382 and 384 will be opened. Opening valve 382 permits the FBP/FSP to flow to the PIT while opening of the vent valve 384 allows excess carrier gas to be vented from the dispersed gas stream so that the amount of breathing gas delivered to the patient from the dispersion gas stream is reduced relative to the amount being delivered through the breathing gas stream from the ventilator.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below. Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for delivering frozen biologic particles (FBP) to a bronchus of a lung of a patient, said method comprising:
    delivering a breathing gas stream to the bronchus of the lung of the patient; and
    delivering FBP from an FBP source to the bronchus of the lung, wherein the FBP comprise a biologic material having an aqueous phase wherein the aqueous phase is frozen so that the material is formed into flowable particles having a size in the range from 4 µm to 100 µm, wherein the particles are capable of being carried into the lower lung of a patient by normal or induced respiration;
    wherein the FBP are entrained in the breathing gas and carried by the breathing gas into the bronchus of the lung, wherein at least a portion of the aqueous phase of the FBP remains frozen as solid ice while being delivered to the bronchus of the lung and thaws only after the FBP are released into the lung.

2. A method as in claim 1 wherein the FBP are frozen while in the FBP source and remain frozen while they are delivered and until they are released into the bronchus of the lung.

3. A method as in claim 1 wherein the breathing gas and the FBP are delivered through separate lumens of a breathing tube.

4. A method as in claim 1 wherein the breathing gas and the FBP are delivered through a common lumen in a breathing tube.

5. A method as in claim 1 wherein the breathing gas and the FBP are delivered during at least a portion of some of the patient's inhalation cycles but not during the patient's exhalation cycles.

6. A method as in claim 1 wherein delivering FBP to the bronchus of the lung comprises providing a bolus of FBP and flowing a volume of carrier gas through the bolus to entrain the FBP in the flowing carrier gas to produce an FBP-entrained flowing carrier gas stream which is delivered to the lung through a FBP lumen separate from the breathing gas.

7. A method as in claim 6 further comprising venting a portion of the carrier gas from the FBP-entrained flowing carrier gas stream to produce a gas reduced FBP-entrained flowing carrier gas stream, wherein said gas reduced FBP-entrained flowing carrier gas stream is delivered to the FBP lumen.

8. A method for delivering frozen biologic particles (FBP) to a bronchus of a lung of a patient, said method comprising:
    dispersing a plurality of boluses of FBP into a flowing carrier gas to entrain the FBP in the flowing carrier gas to produce an FBP-entrained flowing carrier gas stream, wherein the FSB comprise a biologic material having an aqueous phase wherein the aqueous phase is frozen so that the material is formed into flowable particles having a size in the range from 4 m to 100 m, wherein the particles are capable of being carried into the lower lung of a patient by normal or induced respiration;
    delivering the FBP-entrained flowing carrier gas stream to the bronchus of the lung of the patient simultaneously with a separate breathing gas stream in synchrony with the patient's inhalation cycle, wherein at least a portion of an aqueous content of the FBP remains frozen while being delivered having undergone a phase change from liquid water to solid ice.

9. A method as in claim 8 wherein a single bolus is delivered with each inhalation, wherein an amount of FBP is controlled by adjusting the inhalation rate delivered by a ventilator.

10. A method as in claim 8 wherein the amount of FBP delivered to the patient is controlled by adjusting an amount of FBP in individual boluses.

11. A method as in claim 10 wherein a tidal volume of breathing gas delivered to the patient comprises a sum of a breathing gas volume and a carrier gas volume delivered on each inhalation cycle.

12. A method as in claim 11 wherein the tidal volume of total breathing gas delivered to the patient is adjusted to a target level by venting a portion of the carrier gas from the FBP-entrained flowing carrier gas stream after dispersing the FBP therein and before delivering the FBP-entrained flowing carrier gas stream and separate breathing gas stream to the bronchus of the lung of the patient to produce a reduced FBP-entrained flowing carrier gas stream.

13. A method as in claim 12 wherein the target level of tidal volume of total breathing gas is in the range from 150 ml to 1000 ml per inhalation cycle.

14. A method as in claim 4 wherein a controller adjusts an amount or rate of delivery of the FBP from the FBP source through the at least one lumen of the breathing tube.

15. A method as in claim 1 wherein the FBP source comprises an external source of frozen biological particles.

16. A method as in claim 14 wherein the controller vents at least 50% of the gas originally present in the FBP-entrained flowing carrier gas stream to produce the gas reduced FBP-entrained flowing carrier gas stream.

17. A method as in claim 1 wherein the biologic material comprises stem cells which remain viable after being released in the bronchus of the lung while still frozen and thereafter carried into the lower lung by normal or induced respiration.

18. A method as in claim 1 further comprising delivering frozen saline particles (FSP) from an FSP source to the bronchus of the lung.

19. A method as in claim 18 wherein the FSP are delivered concurrently with the FBP.

20. A method as in claim 19 wherein the FSP are delivered in the same breathing gas stream as the FBP.

21. A method as in claim 19 further comprising delivering a second breathing gas stream to the bronchus of the lung of the patient, wherein the FSP are entrained in the second breathing gas stream.

22. A method as in claim 1 wherein the FBP are delivered through a thermally insulated lumen.

* * * * *